(12) United States Patent
Starrett et al.

(10) Patent No.: US 8,692,042 B2
(45) Date of Patent: Apr. 8, 2014

(54) METHODS FOR PRODUCING CYCLOHEPTATRIENE

(75) Inventors: Richmond M. Starrett, Baton Rouge, LA (US); Christopher D. Claeboe, Hamilton, MI (US); Anthony F. Skufca, Zachary, LA (US); Joseph H. Miller, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 13/583,306

(22) PCT Filed: Feb. 22, 2011

(86) PCT No.: PCT/US2011/025646
§ 371 (c)(1),
(2), (4) Date: Sep. 17, 2012

(87) PCT Pub. No.: WO2011/123198
PCT Pub. Date: Oct. 6, 2011

(65) Prior Publication Data
US 2013/0066127 A1  Mar. 14, 2013

Related U.S. Application Data

(60) Provisional application No. 61/319,638, filed on Mar. 31, 2010.

(51) Int. Cl.
C07C 1/28 (2006.01)
C07C 1/26 (2006.01)

(52) U.S. Cl.
USPC .......................................... 585/359; 585/357

(58) Field of Classification Search
USPC .................................................. 585/359, 357
See application file for complete search history.

(56) References Cited

U.S. PATENT DOCUMENTS 2,831,906 A  4/1958 Winberg

FOREIGN PATENT DOCUMENTS

RU  2 285 689 C1  10/2006

OTHER PUBLICATIONS

Robinson: "Pyrolytic conversion of 7, 7-dichloronorcarane" Journal of Organic Chemistry., vol. 29, Jan. 1, 1964, pp. 3433-3434, XP002633606, US American Chem.

*Primary Examiner* — Thuan D Dang
(74) *Attorney, Agent, or Firm* — Marcy M. Hoefling; James A. Jubinsky; Nathan C. Dunn

(57) ABSTRACT

This invention relates to methods for producing cycloheptatriene from at least 7,7-dichloronorcarane and a liquid component comprising a $C_8$ to $C_{30}$ succinic anhydride, a carboxylic acid, or a $C_8$ to $C_{30}$ alkyldimethylamine at about 205 deg. C. to about 230 deg. C.

7 Claims, 1 Drawing Sheet

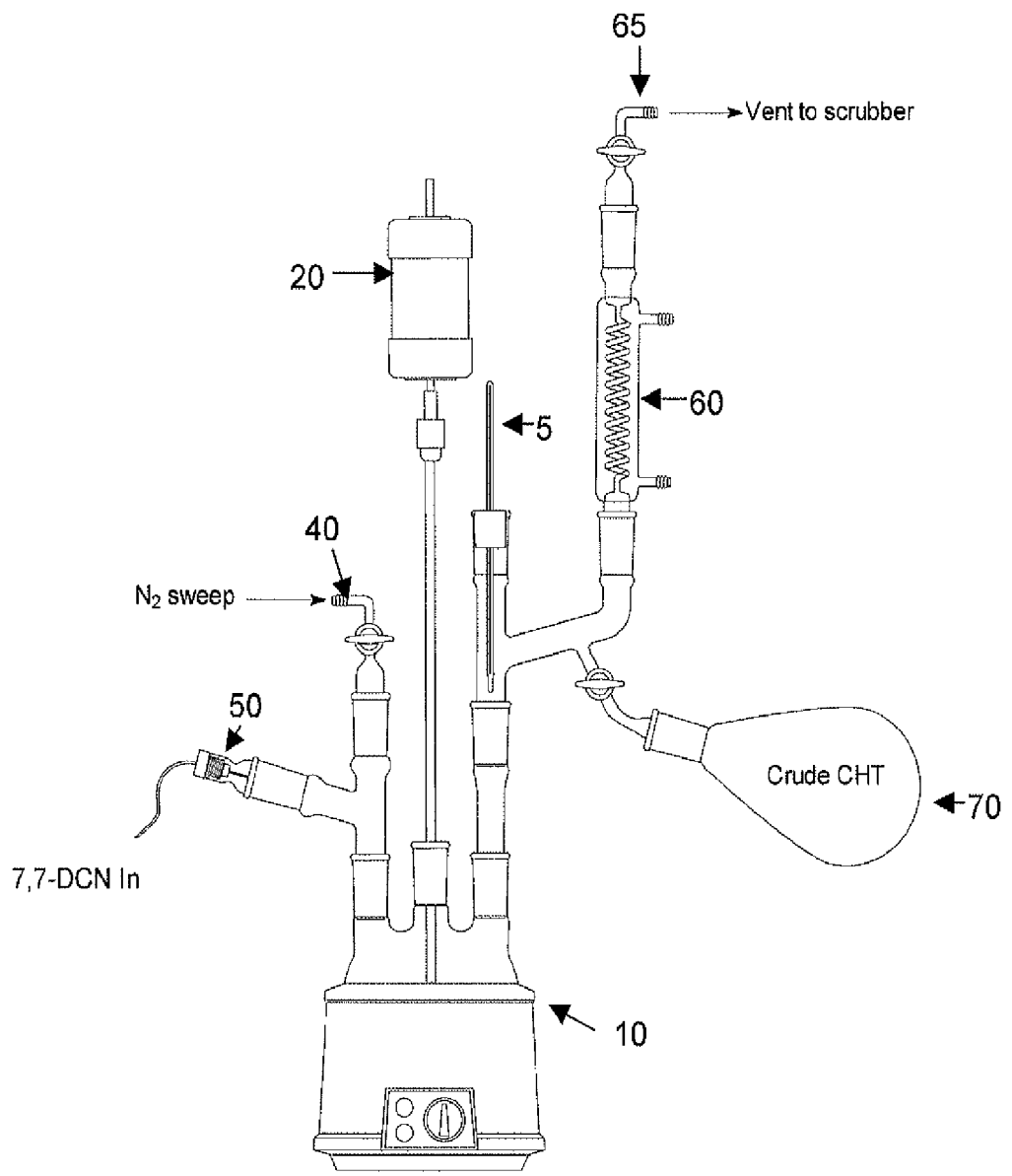

METHODS FOR PRODUCING CYCLOHEPTATRIENE

BACKGROUND

Cycloheptatriene is widely used as a ligand in organometallic chemistry and as a building block in organic syntheses. Known methods for producing cycloheptatriene, in particular methods using 7,7-dichloronorcarane as raw material, require high temperatures, usually in excess of 400 deg. C., and, thus, much energy for obtaining and maintaining the high temperatures and expensive equipment for surviving the high temperatures with repeated use.

Therefore, a need exists for improved methods for producing cycloheptatriene.

THE INVENTION

This invention satisfies the above-defined needs by providing methods for producing cycloheptatriene comprising (a) combining at least 7,7-dichloronorcarane and a liquid component in a container to form a reaction combination, wherein the container has a gas inlet and a gas vent, and the liquid component comprises a $C_8$ to $C_{30}$ succinic anhydride, a carboxylic acid, or a $C_8$ to $C_{30}$ alkyldimethylamine; (b) while passing gaseous nitrogen through the reaction combination in the container via the gas inlet and the gas vent at a rate up to about 100 mL/min, heating the reaction combination to, and maintaining the reaction combination at, about 205 deg. C. to about 230 deg. C.; (c) collecting distillate from the container; and (d) obtaining cycloheptatriene from the distillate. This invention also comprises such methods wherein in (b) HCl is produced in the reaction combination and substantially all of the produced HCl is vented via the gas vent, and such methods wherein the distillate comprises substantially no 7,7-dichloronorcarane, e.g., less than about 1 vol % 7,7-dichloronorcarane, up to about 50 vol % 7,7-dichloronorcarane.

FIGURES

The invention will be better understood by reference to the FIGURE (FIG. 1), which illustrates a method according to this invention.

DESCRIPTION

The basic equation for CHT synthesis in accordance with this invention is as follows:

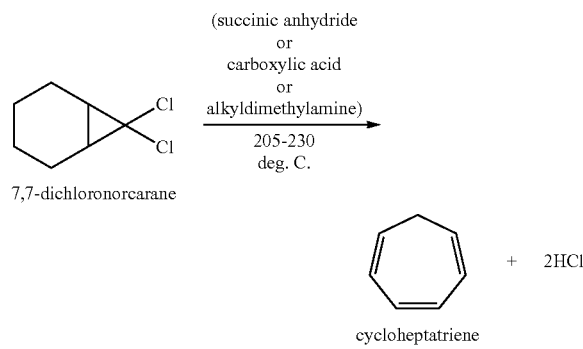

$C_8$ to $C_{30}$ Succinic anhydrides suitable for use in methods of this invention include $C_8$ to $C_{30}$ alkenyl succinic anhydrides, e.g., $C_{16}$ alkenyl succinic anhydrides. $C_8$ to $C_{30}$ Alkyldimethylamines suitable for use in methods of this invention include $C_{16}$ alkyldimethylamines. Suitable carboxylic acids for use in methods of this invention include long, short, and/or branched carboxylic acids. For example, cyclohexane carboxylic acid is suitable for use in this invention.

In methods of this invention, the reaction combination is heated to, and maintained at, about 205 deg. C. to about 230 deg. C., or about 210 deg. C. to about 225 deg. C., or about 215 deg. C. to about 220 deg. C.

In methods of this invention, all, or substantially all, of the produced gaseous HCl is removed from the pyrolysis reaction in order to obtain CHT samples bearing minimized quantities of toluene while concomitantly increasing the isolated yield. In addition, the nitrogen purge is adjusted to such a rate as to effectively flush HCl from the reaction combination while simultaneously minimizing 7,7-DCN from collecting in the distillate. Methods of this invention can be conducted under batch conditions or under semi-continuous conditions. In addition, vacuum distillation of the distillate from the container can be used to effect nearly complete removal of residual 7,7-DCN.

EXAMPLES

The following examples are illustrative of the principles of this invention. It is understood that this invention is not limited to any one specific embodiment exemplified herein, whether in the examples or the remainder of this patent application.

Example 1

To a 1000-mL, 4-neck round bottom flask fitted with a mechanical stirrer, nitrogen purge line and distillation condenser leading to a caustic scrubber was added 276.5 g of $C_{16}$-ASA ($C_{16}$ alkenyl succinic anhydride) followed by 187.5 g (1.14 mol) of 7,7-dichloronorcarane. The stirred mixture was heated to approximately 220 deg. C. under a slight nitrogen purge (1-2 bubbles/sec observed in the scrubber). The distillate was collected as it was formed in the distillation adapter. After 9 hours, the reaction was allowed to cool. The cycloheptatriene thus obtained was isolated as a pale yellow liquid: crude yield 81.6 g (0.886 mol, 81.6%).

Example 2

A 3-L, 4-neck round-bottom flask 10 was equipped with a mechanical stirrer 20, thermocouple 5, nitrogen inlet 40, MASTERFLEX addition pump 50 and a distillation head 60 with associated distillate collection flask 70 and vent 65 (see the FIGURE (FIG. 1)). The flask 10 was charged with 762 g $C_{16}$-ASA followed by 605 g of 7,7-DCN via MASTERFLEX addition pump 50. The nitrogen sweep rate via nitrogen inlet 40 and vent 65 was set at approximately 100 mL/min and the mixture was heated to approximately 215 deg. C. Once CHT collection in collection flask 70 was evident, the DCN addition via the MASTERFLEX addition pump 50 was continued at a rate of approximately 1.4 g/min. After 96-hr, the reaction was halted. Total processed 7,7-DCN was 5.4 kg resulting in a total of 2.2 kg crude CHT collected (73% crude yield).

This invention is advantageous in that it provides methods for producing cycloheptatriene at temperatures of about 205-230 deg. C. or 210-225 deg. C., which is much lower than the temperatures of known processes, which require in excess of 400 deg. C. The benefits are that less energy is required to heat and maintain the temperature of the reactants and use of expensive equipment capable of withstanding the excessive temperatures of known methods is not required. Additionally, this invention facilitates the reduction of toluene formation by using a nitrogen sweep to eject the HCl by-product.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

While the present invention has been described in terms of one or more preferred embodiments, it is to be understood that other modifications may be made without departing from the scope of the invention, which is set forth in the claims below.

What is claimed is:

1. A method for producing cycloheptatriene comprising:
   (a) combining at least 7,7-dichloronorcarane and a liquid component in a container to form a reaction combination, wherein the container has a gas inlet and a gas vent, and the liquid component comprises a $C_8$ to $C_{30}$ succinic anhydride, a carboxylic acid, or a $C_8$ to $C_{30}$ alkyldimethylamine;
   (b) while passing gaseous nitrogen through the reaction combination in the container via the gas inlet and the gas vent at a rate up to about 100 mL/min, heating the reaction combination to, and maintaining the reaction combination at, about 205 deg. C. to about 230 deg. C.;
   (c) collecting distillate from the container; and
   (d) obtaining cycloheptatriene from the distillate.

2. The method of claim 1 wherein the liquid component comprises a $C_8$ to $C_{30}$ alkenyl succinic anhydride.

3. The method of claim 1 wherein the liquid component comprises a $C_{18}$ alkenyl succinic anhydride.

4. The method of claim 1 wherein the liquid component comprises a carboxylic acid.

5. The method of claim 1 wherein the liquid component comprises a $C_{16}$ alkyldimethylamine.

6. The method of claim 1 wherein in (b) HCl is produced in the reaction combination and substantially all of the produced HCl is vented via the gas vent.

7. The method of claim 1 wherein the distillate comprises less than about 1 vol % up to about 50 vol % 7,7-dichloronorcarane.

* * * * *